United States Patent
Schmigalle et al.

(10) Patent No.: US 9,957,205 B2
(45) Date of Patent: May 1, 2018

(54) PLANT AND METHOD FOR PRODUCING ETHYLENE

(71) Applicant: LINDE AKTIENGESELLSCHAFT, Munich (DE)

(72) Inventors: Holger Schmigalle; Volker Göke, Geretsried (DE); Christian Thaller, Munich (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 0 days. days.

(21) Appl. No.: 14/427,456

(22) PCT Filed: Sep. 18, 2013

(86) PCT No.: PCT/EP2013/002809
§ 371 (c)(1),
(2) Date: Mar. 11, 2015

(87) PCT Pub. No.: WO2014/044387
PCT Pub. Date: Mar. 27, 2014

(65) Prior Publication Data
US 2015/0246856 A1    Sep. 3, 2015

(30) Foreign Application Priority Data

Sep. 20, 2012 (DE) .......................... 10 2012 018 602
Dec. 6, 2012 (EP) ..................................... 12008169

(51) Int. Cl.
*C07C 2/84* (2006.01)
*C07C 4/04* (2006.01)
(Continued)

(52) U.S. Cl.
CPC ............ *C07C 2/84* (2013.01); *B01J 19/2445* (2013.01); *C01B 3/382* (2013.01); *C07C 4/04* (2013.01);
(Continued)

(58) Field of Classification Search
CPC ... C07C 4/04; C07C 2/84; C07C 11/04; B01J 19/2445; C10G 9/36; C01B 3/382
See application file for complete search history.

(56) References Cited

U.S. PATENT DOCUMENTS 5,118,898 A * 6/1992 Tyler ......................... B01J 21/16
                                                       585/500
5,254,781 A * 10/1993 Calamur .................. B01J 8/009
                                                       585/500
(Continued)

FOREIGN PATENT DOCUMENTS

DE       15 43 156 A1     7/1969
DE       32 37 079 A1     4/1984
(Continued)

*Primary Examiner* — Brian A McCaig
*Assistant Examiner* — Jason Y Chong
(74) *Attorney, Agent, or Firm* — Millen White Zelano & Branigan, PC

(57) ABSTRACT

A plant for producing ethylene having a reactor to effect oxidative coupling of methane, a work-up unit connected to the reactor to separate a first material stream produced by the reactor into a $C_{1-}$ material stream and an ethylene product stream and a separation unit connected to the work-up unit to separate the $C_{1-}$ material stream into a hydrogen-rich product stream and a hydrogen-lean residual gas stream. The plant also includes a steam cracker to produce (5) for producing an olefin-containing and hydrogen-containing crude gas stream. The steam cracker is connected to the work-up unit that separates the crude gas stream along with the first material stream into the $C_{1-}$ material stream and the ethylene product stream. A portion of the residual gas stream is recycled to the reactor. A process for producing ethylene using the plant is also described.

4 Claims, 1 Drawing Sheet

(51) Int. Cl.
  *B01J 19/24* (2006.01)
  *C01B 3/38* (2006.01)
  *C10G 9/36* (2006.01)

(52) U.S. Cl.
  CPC ............ *C10G 9/36* (2013.01); *B01J 2219/24* (2013.01); *C01B 2203/0216* (2013.01); *C01B 2203/0261* (2013.01); *C01B 2203/043* (2013.01); *C01B 2203/1247* (2013.01); *C01B 2203/141* (2013.01); *C01B 2203/146* (2013.01); *C10G 2300/1044* (2013.01); *C10G 2400/20* (2013.01); *C10G 2400/24* (2013.01); *Y02P 30/40* (2015.11)

(56) References Cited

U.S. PATENT DOCUMENTS

| | | | | |
|---|---|---|---|---|
| 5,785,739 A | * | 7/1998 | Baker | .................. B01D 53/002 95/266 |
| 2010/0249473 A1 | * | 9/2010 | Butler | ........................ C07C 2/82 585/324 |
| 2014/0012053 A1 | * | 1/2014 | Iyer | ........................... C07C 2/84 585/302 |

FOREIGN PATENT DOCUMENTS

| | | |
|---|---|---|
| DE | 43 33 372 A1 | 4/1994 |
| NL | 9 300 168 A | 5/1994 |
| WO | WO 2007/045364 A2 | 4/2007 |

\* cited by examiner

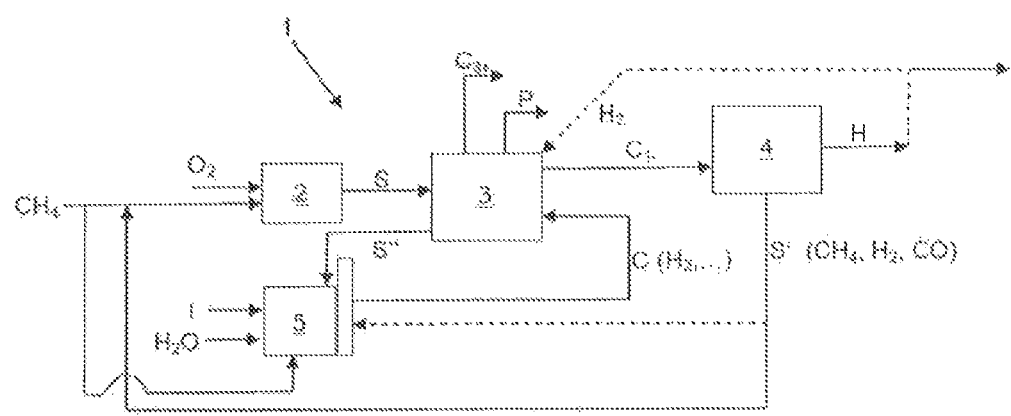

PLANT AND METHOD FOR PRODUCING ETHYLENE

FIELD OF THE INVENTION

The invention relates to a plant for producing ethylene, in particular by oxidative coupling of methane. The invention further relates to a process for producing ethylene.

BACKGROUND OF THE INVENTION

One known type of plant for producing ethylene comprises a reactor into which oxygen and methane are introduced to effect oxidative coupling of methane. In this reaction methyl radicals are initially formed at high temperatures (about 600-880° C.) over a catalytic surface (e.g. two- or multicomponent metal oxide catalyst comprising alkali elements, alkaline earth elements and/or elements selected from the group of rare earths) in the reactor. The methyl radicals then recombine in the gas phase to form ethane which is converted into ethylene in the further course of the reaction. A first material stream comprising at least ethane and ethylene is obtained as a result. The plant further comprises a work-up unit fluidly connected to the reactor and configured to separate the first material stream into at least a $C_{1-}$ material stream and an ethylene product stream. The $C_{1-}$ material stream comprises hydrocarbons having one carbon atom and CO and $H_2$. The plant further comprises a separator (e.g. pressure swing adsorber) connected to the work-up unit and configured to separate the $C_{1-}$ material stream into a hydrogen-rich hydrogen product stream and a hydrogen-lean residual gas stream which is typically fired. A method and apparatus for the catalytic conversion of methane to hydrocarbons having at least two carbon atoms is described in NL9300168.

Another existing method of ethylene or olefin preparation is steam cracking. This method comprises mixing a hydrocarbon-containing input with steam and typically passing the input gas thus formed through metallic tubes of a cracking furnace to effect cracking. The tubes are externally heated with burners to provide the necessary heat for the endothermic cracking process. The olefin-containing and hydrogen-containing crude gas stream thus obtained is typically purified and fractionated into the desired olefins, in particular ethylene.

There remains a need in the art for improvements to a plant and a process of ethylene production.

SUMMARY OF THE INVENTION

The invention combines the features of an Oxidative Coupling of Methane (OCM) reactor and a steam cracker to improve ethylene production.

BRIEF DESCRIPTION OF THE DRAWING

The drawing FIGURE is a schematic diagram of a plant and a process according to the invention for producing ethylene.

DETAILED DESCRIPTION OF THE INVENTION

According to the invention a steam cracker for producing an olefin-containing and hydrogen-containing crude gas stream is connected to the work-up unit of an OCM plant. The work-up unit is configured to separate the crude gas stream along with the first material stream from the reactor of the OCM plant into at least the $C_{1-}$ material stream and the ethylene product stream. The plant is configured to recycle at least a portion of the residual gas stream from the separator of the OCM plant into the OCM reactor as input. The first material stream and the crude gas stream may be combined in the work-up unit and the individual streams may be purified prior to being combined. The $C_{1-}$ material stream and the ethylene product stream are then removed from the combined stream.

The combination of an OCM reactor with a steam cracker according to the invention is advantageous since the hydrogen produced in the steam cracking and recycled into the OCM reactor provides energy in the OCM reactor through hydrogen combustion and also activates the catalyst in the reactor and reduces coking in the reactor.

The steam cracker which may comprise one or more cracking furnaces for steam cracking is configured to crack hydrocarbon input, for example ethane, propane, natural gas condensates and/or relatively heavy inputs, for example naphtha, in the presence of steam to form the crude gas stream containing hydrogen and ethylene.

The work-up unit removes from both the first material stream produced during oxidative coupling of methane and the crude gas stream produced during steam cracking an ethane-rich and propane-rich material stream which is injected as input into the steam cracker to which it is fluidly connected.

When the separation unit is fluidly connected to the steam cracker, the plant may be configured to inject at least a portion of the residual gas stream into the steam cracker. This portion of the residual gas stream may be co-fired to provide the heat required for the steam cracking of the aforementioned input (e.g. ethane and/or relatively heavy inputs such as naphtha) or to contribute to the required heat.

The plant according to the invention may moreover be configured to recycle a substream of the hydrogen product stream into the work-up unit in order to hydrogenate hydrocarbons.

The invention also provides a process for producing ethylene.

The process according to the invention comprises introducing oxygen and methane into a reactor, effecting oxidative coupling of methane in the reactor to form a first material stream, steam cracking a hydrocarbon-containing input in a steam cracker to produce an olefin-containing and hydrogen-containing crude gas stream, separating the first material stream along with the crude gas stream into an ethylene product stream and a $C_{1-}$ material stream in a work-up unit, separating the $C_{1-}$ material stream into a hydrogen product stream and a hydrogen-lean residual gas stream in a separation unit and recycling at least a substream of the residual gas stream into the reactor as input.

In addition, an ethane-rich and propane rich material may be removed from the first material stream and/or the crude gas stream with the ethane-rich and propane-rich material stream being passed into the steam cracking as input.

In addition at least a substream of the residual gas stream may be co-fired to produce heat for the steam cracking process.

Further a substream of the hydrogen product stream may be recycled into the work-up unit for use hydrogenating hydrocarbons for example.

An illustrative embodiment of the invention will be described with reference to the drawing figure.

The drawing figure is a schematic diagram of a plant and a process according to the invention for producing ethylene.

The figure shows a plant 1 for preparing ethylene and comprising a reactor 2 for effecting oxidative coupling of methane (known as an OCM reactor), a work-up unit 3, a separation unit (e.g., pressure swing adorber) 4 and a steam cracker 5 comprising at least one cracking furnace.

$CH_4$ and $O_2$ are injected into reactor 2 to effect oxidative coupling of methane at elevated temperatures over a catalyst surface in reactor 2. This forms a first material stream S containing ethylene and ethane.

The steam cracker 5 has an input I consisting of, for example, ethane and/or naphtha. Steam is also injected. The, is cracked in the steam cracker 5 to produce a crude gas stream C containing olefins, in particular ethylene, and hydrogen.

The work-up unit 3 is provided downstream of reactor 2 and receives the optionally prepurified first material stream S and the optionally prepurified crude gas stream C. These streams are combined in the work-up unit 3 and then separated into a $C_{3+}$ material stream (hydrocarbons comprising three or more carbon atoms), an ethylene product stream P, an ethane-rich and propane-rich material stream S" and a $C_{1-}$ material stream, The $C_{1-}$ material stream is injected into separation unit 4 to produce a hydrogen product stream H.

The ethane-rich and propane-rich material stream S" removed in work-up unit 3 is passed into steam cracker 5 as additional input.

The $C_{1-}$ material stream is separated into a hydrogen product stream H and a hydrogen-lean residual gas stream S' in separation unit 4. This may be effected using, for example, pressure swing adsorption in which the $C_{1-}$ material stream is passed through at least one adsorber at elevated pressure. Hydrogen passes through the at least one adsorber to form the hydrogen product stream H. The relatively heavy components, for example $CH_4$ and CO, are adsorbed by the at least one adsorber and then desorbed at a relatively low pressure to provide the hydrogen-lean residual gas stream S'. The residual gas stream S' also contains hydrogen from a substream of the hydrogen product stream H that is used to purge the at least one adsorber.

The residual gas stream S' is then returned to reactor 2 as input. A portion of the residual gas stream S' may be passed into the steam cracker 5 for co-firing to generate the heat required for the steam cracking or to contribute to the required heat. Co firing of the portion of the residual gas stream S' and $CH_4$ diverted upstream of reactor 2 is also possible.

A portion of the hydrogen product stream H may be used to hydrogenate components of the first material stream S and/or of the crude gas stream C in work-up unit 3.

It will be understood that the embodiments described herein are merely exemplary and that one skilled in the art may make variations and modifications without departing from the spirit and scope of the present invention. All such variations and modifications are intended to be included within the scope of the invention as described above. Further, all embodiments disclosed are not necessarily in the alternative, as various embodiments of the invention may be combined to provide the desired result.

LIST OF REFERENCE NUMERALS

1 Plant
2 OCM reactor
3 Work-up unit
4 Separation unit (e.g. pressure swing adsorber)
5 Steam cracker
I Input for steam cracking
S First material stream
S' Hydrogen-containing residual gas stream
S" Ethane- and propane-rich material stream
C Olefin- and hydrogen-containing crude gas stream
P Ethylene product stream
H Hydrogen product stream

The invention claimed is:

1. A method of producing ethylene comprising:
introducing oxygen and methane into a reactor;
effecting oxidative coupling of the methane in the reactor to form a first material stream;
introducing a hydrocarbon-containing input to a steam cracker;
steam cracking the hydrocarbon-containing input in the steam cracker to produce an olefin-containing and hydrogen-containing crude gas stream;
introducing the first material stream and the olefin-containing and hydrogen-containing crude gas stream into a work-up unit;
separating the first material stream and the olefin-containing and hydrogen-containing crude gas stream using the work-up unit into an ethylene product stream and a $C_{1-}$ material stream;
introducing the $C_{1-}$ material stream into a separation unit;
separating the $C_{1-}$ material stream using the separation unit into a hydrogen-rich product stream and a hydrogen-lean residual gas stream;
recycling at least a substream of the hydrogen-lean residual gas stream into the reactor;
recycling at least a substream of the hydrogen-rich product stream into the work-up unit;
removing an ethane-rich and propane-rich material stream from said first material stream and the olefin-containing and hydrogen-containing crude gas stream in the work-up unit; and
recycling the ethane-rich and propane-rich material stream to the steam cracker.

2. The method according to claim 1, further comprising:
recycling at least a substream of the hydrogen-lean residual gas stream to the steam cracker; and
firing the recycled hydrogen-lean residual gas stream in the steam cracker to produce heat for steam cracking.

3. The method according to claim 1, wherein the separating the $C_{1-}$ material stream into the hydrogen-rich product stream and the hydrogen-lean residual gas stream comprises separation by pressure swing adsorption in the separation unit.

4. The method according to claim 1 wherein the hydrocarbon-containing input for the steam cracking is ethane, propane, natural gas condensates or naphtha.

* * * * *